United States Patent
Lum et al.

(10) Patent No.: US 8,012,132 B2
(45) Date of Patent: Sep. 6, 2011

(54) LUER-SNAP CONNECTION AND LUER-SNAP SYRINGE

(75) Inventors: Chee Leong Lum, Pequannock, NJ (US); Ivan Zivkovic, Midland Park, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 12/391,363

(22) Filed: Feb. 24, 2009

(65) Prior Publication Data

US 2010/0217206 A1  Aug. 26, 2010

(51) Int. Cl.
*A61M 5/34* (2006.01)
(52) U.S. Cl. .......................... 604/240; 604/242; 604/243
(58) Field of Classification Search .................. 604/240, 604/242, 243
See application file for complete search history.

(56) References Cited

U.S. PATENT DOCUMENTS

| | | | |
|---|---|---|---|
| 791,802 A | 6/1905 | De Lisle | |
| 1,591,762 A | 7/1926 | Haines | |
| 1,683,349 A | 9/1928 | Hein | |
| 1,683,350 A | 9/1928 | Hein | |
| 2,020,111 A | 11/1935 | Eisele | |
| 2,034,294 A | 3/1936 | Hein | |
| 2,088,338 A | 7/1937 | Popper et al. | |
| 2,158,593 A * | 5/1939 | Scrimgeour | 604/242 |
| 2,764,978 A | 10/1956 | Everett | |
| 2,834,346 A * | 5/1958 | Adams | 604/242 |
| 2,902,995 A | 9/1959 | Loper | |
| 3,043,304 A | 7/1962 | Higgins | |
| 3,179,107 A | 4/1965 | Clark | |
| 3,469,581 A | 9/1969 | Burke | |
| 3,491,757 A | 1/1970 | Arce | |
| 4,040,421 A | 8/1977 | Young | |
| 4,281,653 A | 8/1981 | Barta et al. | |
| 4,430,080 A | 2/1984 | Pasquini et al. | |

(Continued)

FOREIGN PATENT DOCUMENTS

EP  1704840 A1  9/2006

OTHER PUBLICATIONS

International Search Report and Written Opinion for PCT/US2010/025147, dated Jun. 4, 2010, 14 pgs.

*Primary Examiner* — Theodore J Stigell
*Assistant Examiner* — Brandy C Scott
(74) *Attorney, Agent, or Firm* — Jeanne P. Lukasavage; Diehl Servilla LLC

(57) ABSTRACT

Syringe having a snap-fit mechanism for attaching a needle hub to a syringe barrel in a snap-fit relationship and packaged medical device comprising a syringe with a snap-fit mechanism and a needle hub are provided. An exemplary syringe includes a barrel with a collar and a rotatable arm which allows connection of a needle hub to the barrel in a snap-fit relationship. Additional features of the collar and rotatable arm may also permit disconnection of the needle hub from the barrel without the use of relative rotation of the needle hub and barrel. In a specific configuration, the syringe utilizes a torsional snap-fit element to connect the needle hub to the barrel in a snap-fit rotation. In a more specific configuration, the syringe utilizes a collar with differing interior surfaces which permit snap-fit assembly and disassembly of the needle and the barrel.

14 Claims, 15 Drawing Sheets

U.S. PATENT DOCUMENTS

| | | |
|---|---|---|
| 4,490,142 A | 12/1984 | Silvern |
| 4,589,871 A | 5/1986 | Imbert |
| 4,675,020 A | 6/1987 | McPhee |
| 4,747,839 A | 5/1988 | Tarello et al. |
| 4,822,343 A | 4/1989 | Beiser |
| 5,047,021 A | 9/1991 | Utterberg |
| 5,053,015 A | 10/1991 | Gross |
| 5,066,287 A | 11/1991 | Ryan |
| 5,205,833 A | 4/1993 | Harsh |
| 5,312,377 A | 5/1994 | Dalton |
| 5,348,544 A | 9/1994 | Sweeney et al. |
| 5,405,340 A | 4/1995 | Fageol et al. |
| 5,458,580 A | 10/1995 | Hajishoreh |
| 5,466,223 A | 11/1995 | Bressler et al. |
| 5,584,818 A | 12/1996 | Morrison |
| 5,611,786 A | 3/1997 | Kirchhofer et al. |
| 5,637,101 A | 6/1997 | Shillington |
| 5,681,295 A | 10/1997 | Gyure et al. |
| 5,713,876 A | 2/1998 | Bogert et al. |
| 5,830,189 A | 11/1998 | Chang |
| 5,836,919 A | 11/1998 | Skurka et al. |
| 5,851,201 A | 12/1998 | Ritger et al. |
| 5,913,846 A | 6/1999 | Szabo |
| 6,132,402 A | 10/2000 | Tessmann et al. |
| 6,217,560 B1 | 4/2001 | Ritger et al. |
| 6,361,525 B2 | 3/2002 | Capes et al. |
| 6,436,076 B1 | 8/2002 | Hsu |
| 7,115,114 B2 | 10/2006 | Caizza |
| 7,217,258 B2 | 5/2007 | Caizza |
| 7,220,573 B2 | 5/2007 | Shea et al. |
| 2002/0138045 A1 | 9/2002 | Moen |
| 2003/0060760 A1* | 3/2003 | Botich et al. .......... 604/110 |
| 2004/0097884 A1* | 5/2004 | Capes et al. .......... 604/240 |
| 2005/0277896 A1 | 12/2005 | Messerli et al. |

* cited by examiner

LUER-SNAP CONNECTION AND LUER-SNAP SYRINGE

TECHNICAL FIELD

Aspects of the present invention relate to syringes having luer snap mechanism for connection to a needle hub in a snap-fit relationship, syringes with a mechanism for attachment of a needle hub to a syringe barrel in a snap-fit relationship without the use of rotational forces and detachment of the needle hub, and packaged medical devices comprising a needle hub and a syringe for connecting to a needle hub in a snap-fit relationship.

BACKGROUND

Syringes and other medical devices having a luer fitting or connection are often assembled with needle hubs or luer fittings. Two common mechanisms used to connect the needle hubs to the syringes include the "luer lock" and "luer slip" mechanisms.

The luer lock mechanism generally includes a male conical fitting in co-axial relation with an internally threaded collar. A cooperating needle hubs or female luer lock fittings have external lugs for engaging the internally threaded collar of the male conical fitting, upon application of a twisting force or torque force to the needle hub. To complete attachment of the needle hub to the syringe, the twisting force must be continued until the external lugs can no longer be threaded into the internally treaded collar of the male conical fitting. To detach the needle hub from the syringe, a twisting force in the opposite direction must be applied to the needle hub. It has been observed that the male conical tip can break off during application of this twisting force and is lodged in the needle hub, rendering both the needle hub and syringe useless.

The luer slip fitting includes a male conical fitting in coaxial without a collar. Cooperating needle hubs or female luer slip fittings have an internal surface which slides over the external surface of the male conical fitting. The needle hub is attached to the male conical fitting in a friction fit relationship. To attach of the needle hub to the male conical fitting, the user must apply enough force with sliding the needle hub to create a fluid tight relationship between the needle hub and male conical fitting. Failure to securely connect the needle hub and medical device can result in "pop offs," where the unsecured needle hub detaches from the male conical fitting during use.

A syringe with a connection mechanism for connecting a needle hub to the syringe in a "snap-fit" relationship, as defined herein, presents a viable solution to these issues. It would be desirable to provide an alternate mechanism for connecting the needle hub to a syringe or medical device which provides ease of connection with sensory and/or tactile feedback. Further, specific mechanisms which also provide ease of disconnection would also be desirable.

SUMMARY

In this disclosure, a convention is followed wherein the distal end of the device is the end closest to a patient and the proximal end of the device is the end away from the patient and closest to a practitioner.

A luer snap system for use with a needle hub is provided. The luer snap system may be used to connect a needle hub to a syringe or other medical device. Aspects of this invention, which will be described herein, pertain to syringes having a barrel with a sidewall and inside surface that defines a chamber for retaining fluids. The barrel also has an open proximal end and a distal end, with a distal wall. The distal wall of the barrel includes a luer tip with an opening therethrough in fluid communication with the chamber. Reference to the term "luer tip" shall include a fluid tip which is shaped or otherwise dimensioned to an appropriate standard, such as standards specified by the International Standards Organization ("ISO"), for example, luer tip may include a frusto-conically shaped fluid tip. The term "luer tip," as used herein, also includes fluid tips configured to a non-ISO standard dimension.

The syringe also includes an elongate plunger rod with a proximal end and a distal end that is distally and proximally movable within the chamber of the barrel. The plunger or plunger rod includes a proximal end and a distal end and a main body extending from the proximal end to the distal end. The distal end of the plunger may include a separate or integral stopper with a face or wall which forms a fluid-tight engagement with the inside surface of the barrel.

One aspect of the present invention pertains to a syringe comprising a barrel with a mechanism for attaching a needle hub to a barrel in a snap-fit relationship without relative rotation between the needle hub and the barrel.

Reference to the term "snap-fit" shall include a mechanical joint system or configuration where two distinct parts are connected or attached with latching features. The mechanical joint system may include one or more flexible latching features which move aside for engagement with a mating part, followed by return of the latching feature toward its original position. The movement of the latching feature to its original position creates an interference to latch the two parts together. The locking feature may be rigid and may force the corresponding part to flex or rotate for attachment. Snap-fit may also include parts which can be assembled and disassembled without any impact on the individual parts and, therefore, can be repeatedly assembled and disassembled. The snap-fit may optionally also include a permanent snap which prevents disassembly. Examples of snap-fit systems or fittings include torsional snap-fit elements, annular snap-fits and cantilever snap-fits.

As used herein, the term "torsional snap-fit" includes joints or elements in which deflection is due to torsional deformation of the fulcrum and not the result of flexural loads. Torsional snap-fit also refers to a latch that is attached to one end of an arm portion or lever, which rotates around a fulcrum or a torsion bar. In use, a force applied to the end of the arm portion opposite the latch. The force produces rotation of the arm portion and the latch about the fulcrum and allows a protrusion on a mating part or male joint to proceed past the latch. When the force applied to the arm portion is removed, the arm portion and latch return to their initial position, joining the parts or joints. In some examples, the fulcrum is disposed between the latch and the end of the arm portion. Reference to "annular snap-fits" includes joints featuring a male component with a peripheral ridge or other protrusion and a corresponding female component having an undercut grove formed into the inside diameter of the female component. The male component deflects the female component and engages into the undercut grove, at which point the female component returns to a stress-free condition. Reference to "cantilever snap-fits" includes a hook disposed on the end of a cantilever beam which deflects as it is inserted into a corresponding female component. As the hook passes the edge of the female component, the cantilever beam returns to its original shape.

According to one or more embodiments of this first aspect of the invention, the distal end of the barrel includes a mechanism for connecting a female luer fitting, standard luer fitting or a needle hub to the distal end of the barrel. The barrel includes a collar extending from the distal wall and surrounding the luer tip in a coaxial relationship. The collar and luer tip define a channel for receiving a needle hub. The collar also may include a rotatable arm that extends from the collar. In one variant, the rotatable arm may extend inwardly toward the luer tip. The rotatable arm can secure the needle hub to the barrel in a snap-fit relationship by engaging a portion of the needle hub.

The rotatable arm can include a pivot portion disposed on the collar that connecting the rotatable arm to the collar. The rotatable arm can also include an arm portion extending radially outwardly from the pivot portion and a latch for securing the needle hub extending into the channel formed between the collar and the luer tip. The rotatable arm can be configured to permit assembly of the needle hub and collar in a snap-fit relationship without relative rotation between the needle hub and the barrel. In a specific embodiment, the rotatable arm prevents removal of the needle hub from the barrel after engagement with a portion of the needle hub or assembly of the needle hub and the collar. In one or more embodiments, the rotatable arm permits removal of the needle hub from the barrel after engagement with a portion of the needle hub or engagement of the needle hub and the collar. The rotatable arm and the open proximal end of the needle hub can be configured such that, when engaged, application of radial force on the rotatable arm permits removal of the needle hub from the collar. For example, the radial force to permit removal of the needle hub from the barrel may include an inwardly directed radial force or a radial force directed toward the luer tip on the rotatable arm. In another example, the radial force for removal of the needle hub from the barrel includes an outwardly directed radial force or a radial force directed away from the luer tip.

In another embodiment of the present invention, the rotatable arm includes a torsional snap fit element. In such embodiments, the syringe may also include a hub with an open proximal end with an outwardly extending lip positioned to engage the torsional snap-fit element. As the hub advances in the channel formed by the collar and the luer tip, the outwardly extending lip advances past the torsional snap-fit element, thereafter the torsional snap-fit element prevents movement of the outwardly extending lip in the distal direction. The torsional snap-fit element may provide tactile and/or audible indication of the advancement of the outwardly extending lip past the torsional snap-fit element. After engagement between the torsional snap-fit element and the outwardly extending lip, application of an inwardly directed radial force on the torsional snap-fit element permits movement of the outwardly extending lip in the distal direction.

A second aspect of the present invention includes a syringe with means for attaching a standard luer fitting to the distal wall of the barrel. In one or more embodiments, the means may attach the standard luer fitting to the distal wall of the barrel in a snap-fit relationship and may also prevents removal of the standard luer fitting or disengagement of the snap-fit relationship between the standard luer fitting and the distal wall. Exemplary means for attaching the standard luer fitting According to one or more embodiments, the means for attaching the standard luer fitting to the barrel includes a co-axial collar that surrounds the luer tip to form a cavity. The cavity is further configured to receive a standard luer fitting. In a specific embodiment, the co-axial collar may include a first interior surface having a rotatable arm and a latch disposed on the rotatable arm extending from the first interior surface into the cavity and a second interior surface that is free of a rotatable arm or latch. In one or more embodiments, the latch is configured to engage a portion of the standard luer fitting, such as a lip disposed on the proximal end of the standard luer fitting. Upon rotation of the standard luer fitting relative to the co-axial collar to align the portion of the standard luer fitting with the second interior surface, the standard luer fitting is permitted movement in the distal direction and the snap-fit relationship between the standard luer fitting and the collar is released.

The syringe according to the second aspect may further include a standard luer fitting that includes an open proximal end configured to advance into the cavity. The open proximal end of one or more embodiments may also include an outwardly extending lip. In such embodiments, upon advancement of the open proximal end into the cavity, the lip advances past the latch in the proximal direction. The latch prevents movement of the lip in the distal direction. Upon rotation of the standard luer fitting to align the lip with the second interior surface, the lip of the needle hub is permitted movement in the distal direction.

In accordance with the embodiments described herein, the syringe barrel may further include provide audible and/or tactile indication of the snap-fit engagement, connection or relationship between the needle hub and the barrel.

A third aspect of the present invention pertains to a packaged medical device comprising a needle hub and a syringe, as described herein, in a single package.

DETAILED DESCRIPTION

Figure 1:
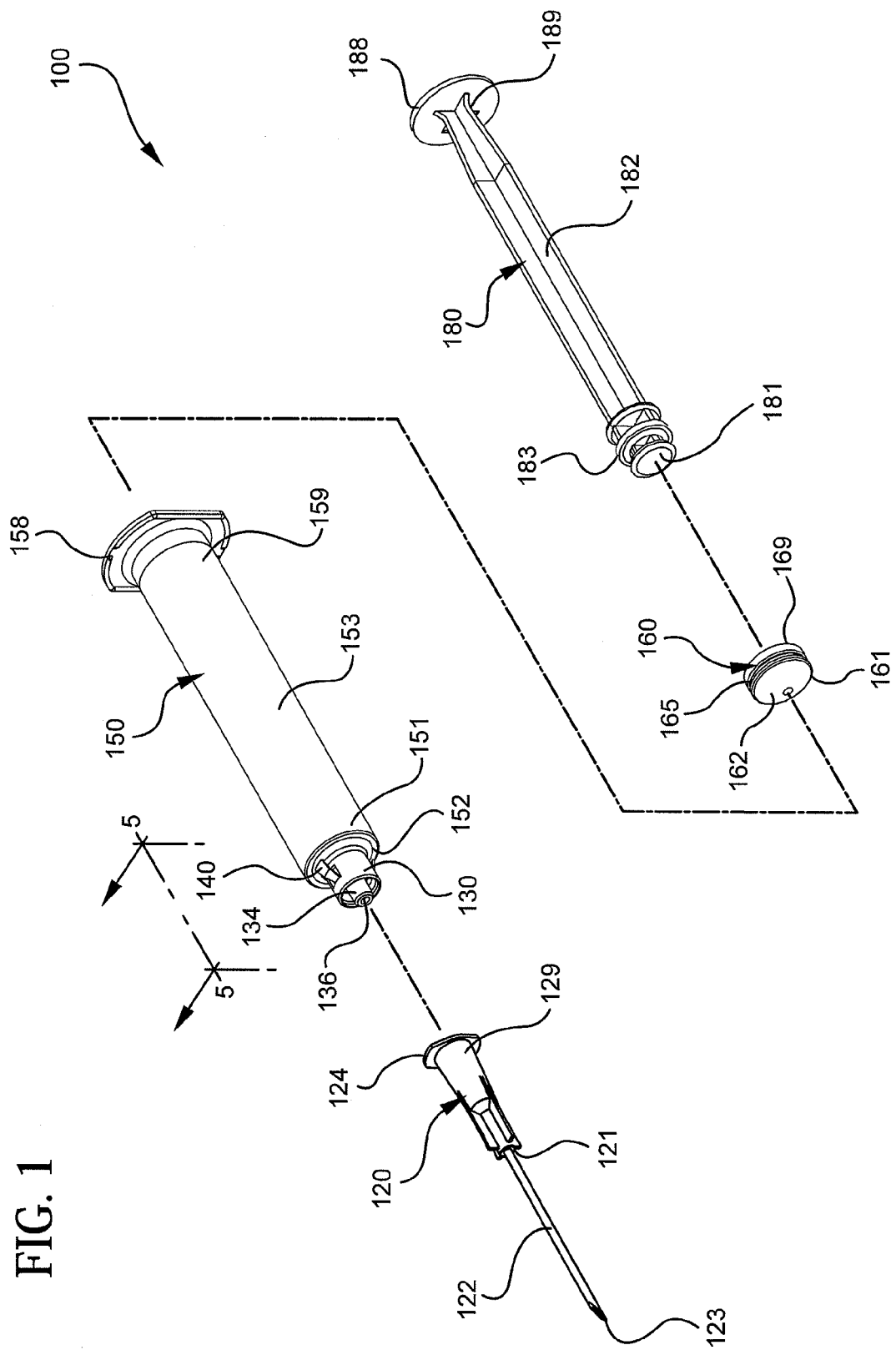
FIG. 1 illustrates a disassembled perspective view of a syringe assembly according to an embodiment of the invention.

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for a syringe including a plunger rod and barrel, which has features and construction which allow the user to attach a needle hub or standard luer fitting to the barrel in a snap-fit relationship or connection.

FIGS. 1-5 show a syringe or syringe assembly 100 having a barrel 150, plunger rod 180 and stopper 160, arranged such that the proximal end of the stopper 169 is attached to the distal end 181 of the plunger rod. The connected stopper 160 and plunger rod 180 are inserted into the proximal end 159 of the barrel 150.

With reference to FIGS. 2-5, the barrel 150 has a cylindrical sidewall 153 with an interior surface 154 that defines a chamber 155. In one embodiment, the chamber 155 holds the contents of the syringe, which may include medication. The barrel 150 includes an open proximal end 159, a distal end 151 and a distal wall 152. The distal wall 152 includes a luer tip 134 having a luer tip opening 136 and a collar 130 defining a channel 132 with the luer tip 134. The collar 130 also includes a rotatable arm 140 and a peripheral gap 138. As will be more fully described herein, the rotatable arm 140 can engage a portion of the needle hub to permit assembly of a needle hub and collar in a snap-fit relationship.

The sidewall 153 of the barrel 150 defines a chamber 155 having a continuous inner diameter along the longitudinal axis of the syringe. Alternatively, the barrel can include a sidewall has an inner diameter, which decreases linearly from the proximal end to the distal end. It is to be understood that the configuration shown is merely exemplary, and the components can be different in shape and size than shown. For example, the barrel can have an exterior prism shape, while retaining a cylindrical interior shape. Alternatively, both the exterior and interior surfaces of the barrel can have non-circular cross-sectional shapes.

The syringe barrel 150 is shown as having a peripheral flange 158 attached at the proximal end 159 of the barrel 150. The syringe shown in FIG. 1 includes an optional needle hub 120 having an open proximal end 129 and a distal end 121, which includes a needle cannula 122 having a lumen 123. When assembled, as shown in FIG. 2, fluid communication is established between the chamber 155 of the barrel 150 through the luer tip opening 136 of the luer tip 134, the needle hub 120 and the lumen 123 of the needle cannula 122.

Figure 2:
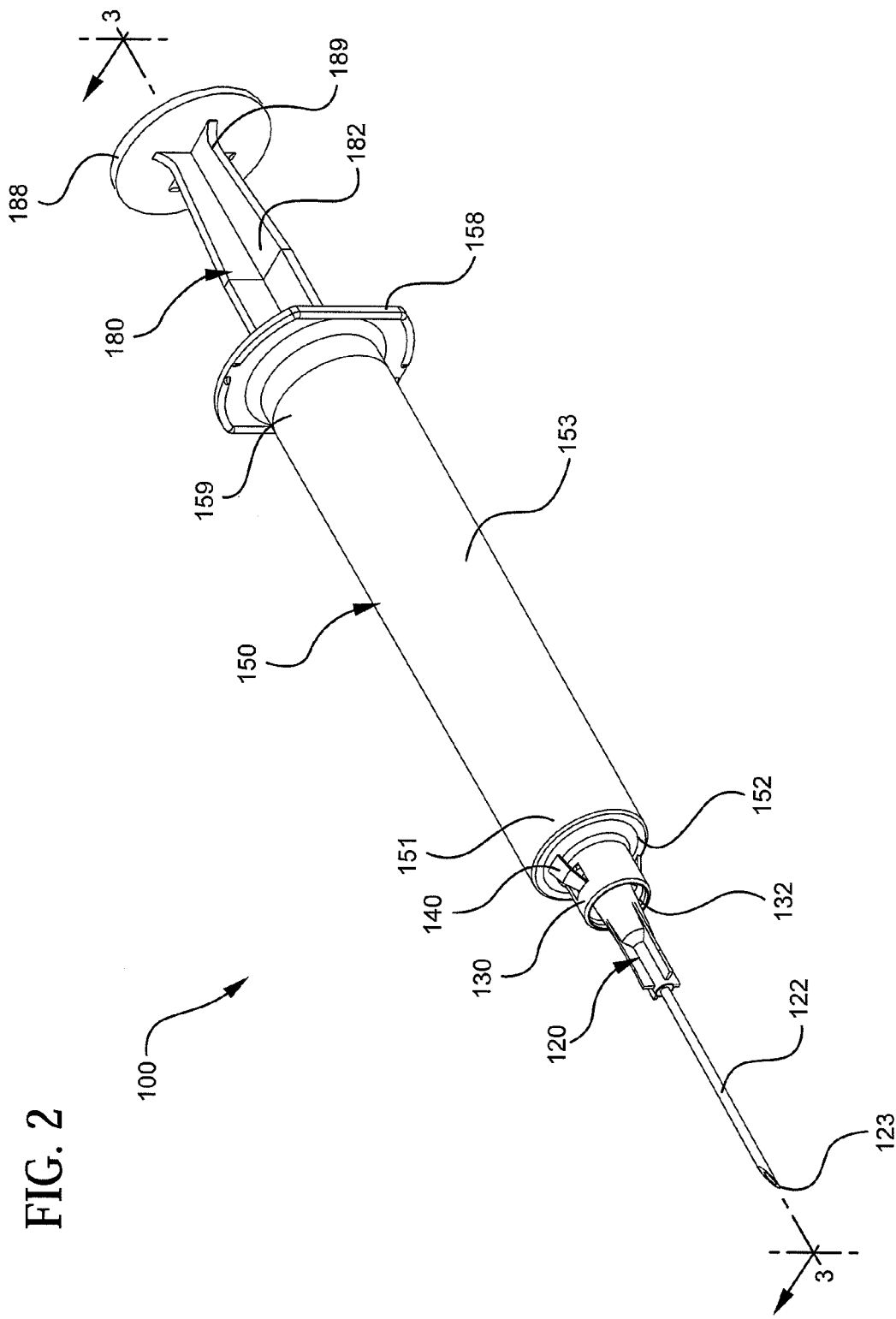
FIG. 2 illustrates a perspective assembled view of the syringe assembly of FIG. 1.

The plunger rod 180 shown in FIG. 1 includes proximal end 189, a distal end 181 and a main body 182 extending between the proximal end 189 to the distal end 191. The plunger rod 180 further includes a thumb press 188 at the proximal end 189 of the plunger rod 180. The distal end 181 of the plunger rod may include a stopper engagement portion 183 for attaching the stopper 160 to the distal end 181 of the plunger rod. The stopper 160 shown in FIG. 1 is a separate component, though it will be understood that the stopper may be integrally formed with the plunger rod in accordance with the embodiments described herein. The stopper 160 includes a distal end 161, a proximal end and a stopper face 162 and sealing edge 165 at the distal end 161 of the stopper 160.

Figure 3:
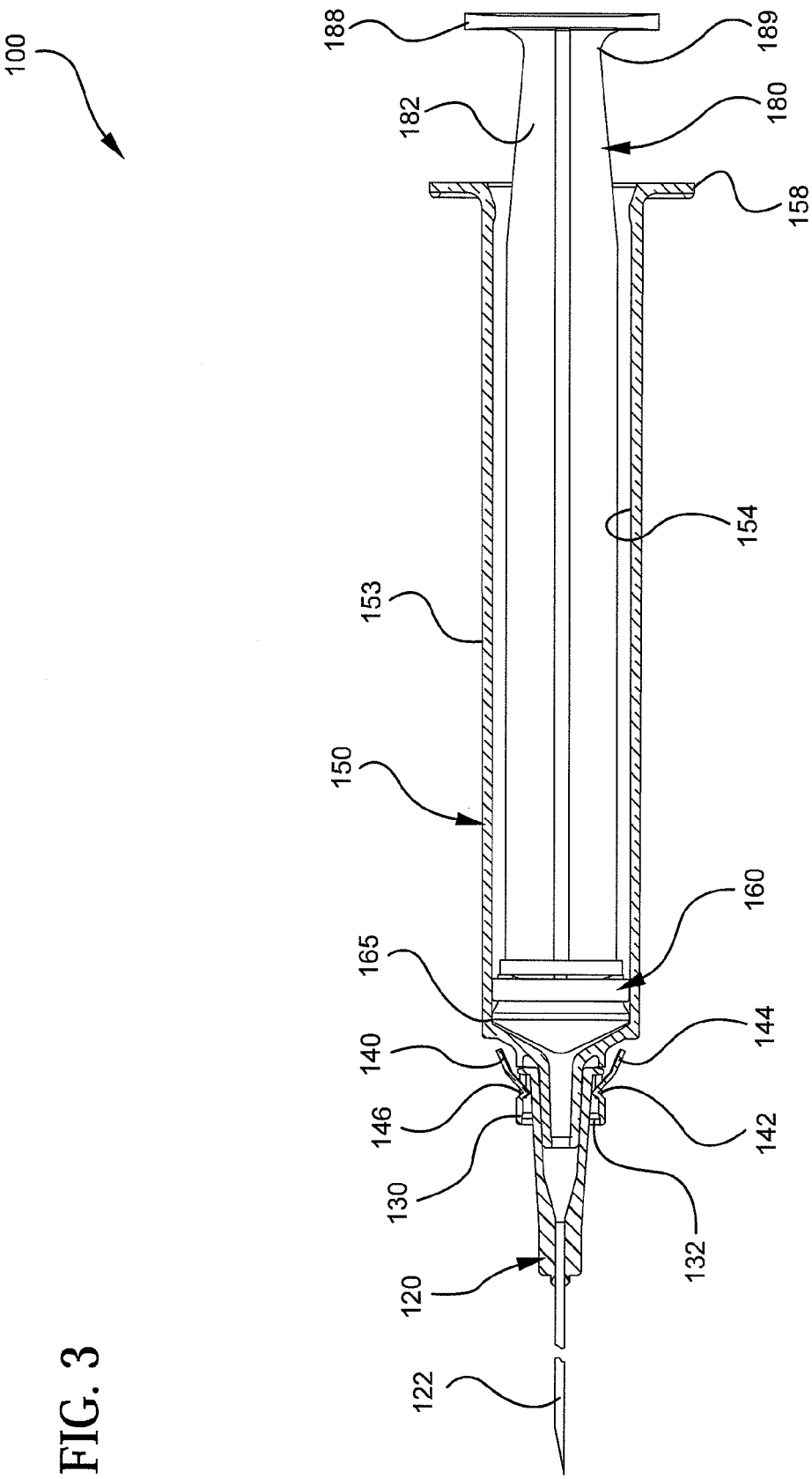
FIG. 3 shows a cross-sectional view of the syringe assembly shown in FIG. 2 taken along line 3-3.
Figure 4:
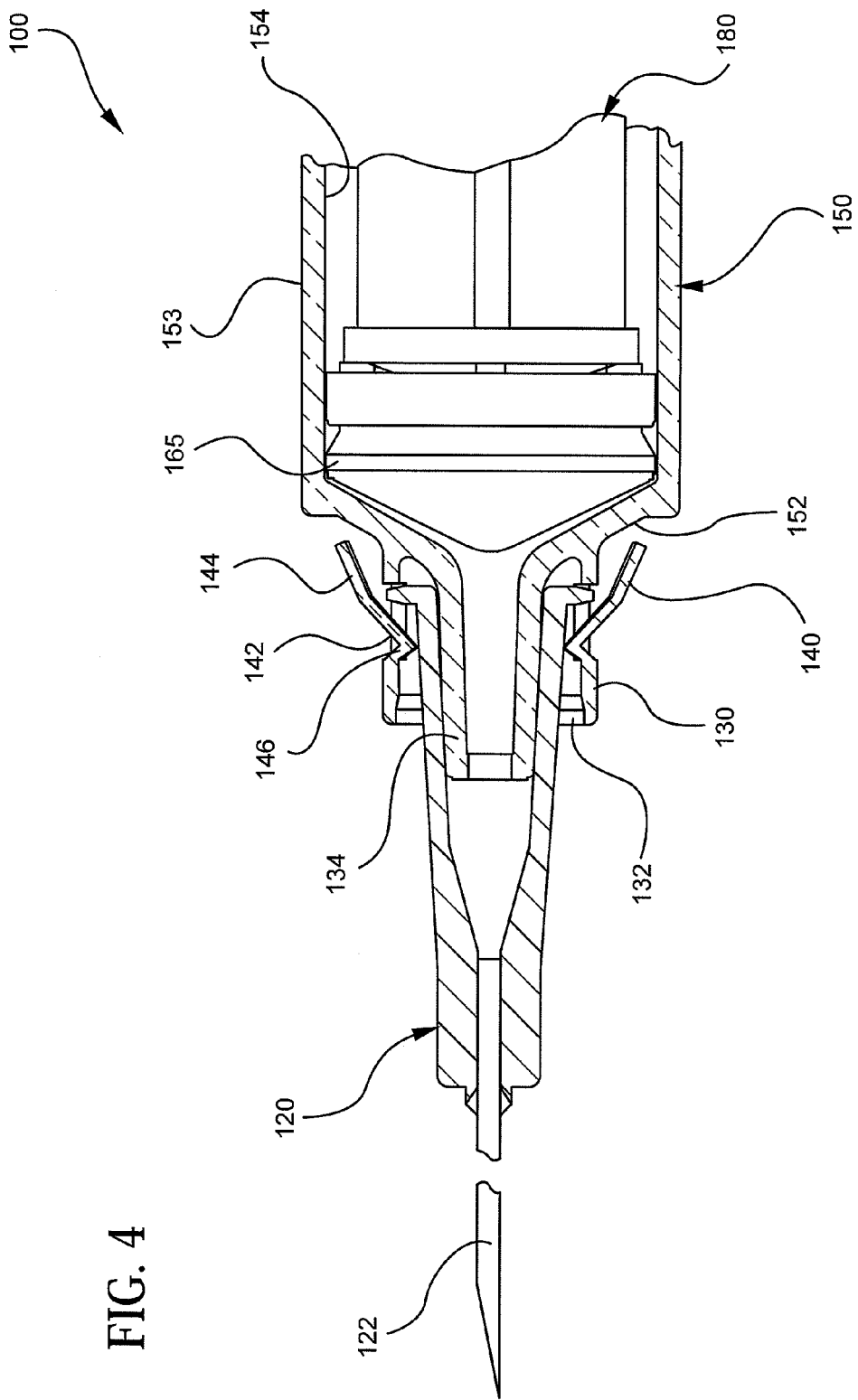
FIG. 4 is an enlarged view of a portion of the barrel shown in FIG. 3.

As more clearly shown in FIGS. 3 and 4, when assembled in a snap-fit relationship, the open proximal end 129 of the needle hub moves into the channel 132 and the rotatable arm 140 engages the open proximal end 129 of the needle hub 120. The rotatable arm 140 shown in FIGS. 1-5 includes a pivot portion 146, extending radially outwardly from the collar 130. The pivot portion 146 provides a fulcrum to allow movement of the rotatable arm 140. The rotatable arm 140 may include an arm portion 144 that moves or rotates about a pivot portion 146. As shown in FIGS. 1-5, the rotatable arm includes a latch 142 between the pivot portion 146 and the arm portion 144. Such an arrangement may be referred to as a second-class lever, wherein when a force applied to the arm portion 144, a resultant force is exerted on the latch 142 or at a location between the arm portion 144 and the pivot portion 146. The pivot portion 146 permits or facilitates movement of the arm portion 144 and the latch 142 radially inwardly or radially outwardly, in relation to the collar. This movement is user actuated, for example, by a practitioner assembling the syringe of FIGS. 1-5.

One skilled in the art would recognize that the barrel shown in FIGS. 1-5 could be used with standard needle hubs or needle hubs which confirm with ISO standards, such as, for example, ISO 594. As shown in FIGS. 1-5, during assembly, a portion of the needle hub 124 (see FIG. 1) at the open proximal end 129 of the needle hub enters the channel 132, moves proximally past the latch 142 of the rotatable arm 140 and into that peripheral gap 138 of the collar 130. In the embodiment shown, the rotatable arm 140 permits a snap-fit relationship between the needle hub and the barrel, without relative rotation. The rotatable arm 140 may further provide an audible and/or tactile indication of the snap-fit engagement or relationship between the needle hub 120 and collar 143. For example, the latch 142 may resist movement of the needle hub 120 into the channel 132 and thereby provide tactile indication or feedback of the proximal movement of the needle hub 120 into the channel 132 and engagement with the rotatable arm 140. The arm portion 146 and latch 142 may alternatively flex as the needle hub 120 travels proximally past the arm portion 144 and latch 142 regain their original position after the needle hub 120 has moved completely into the channel 132. In such embodiments, as the arm portion 144 and latch 142 regain their original position, it may produce audible indication of the engagement of the latch 142 and the needle hub 120.

Figure 5:
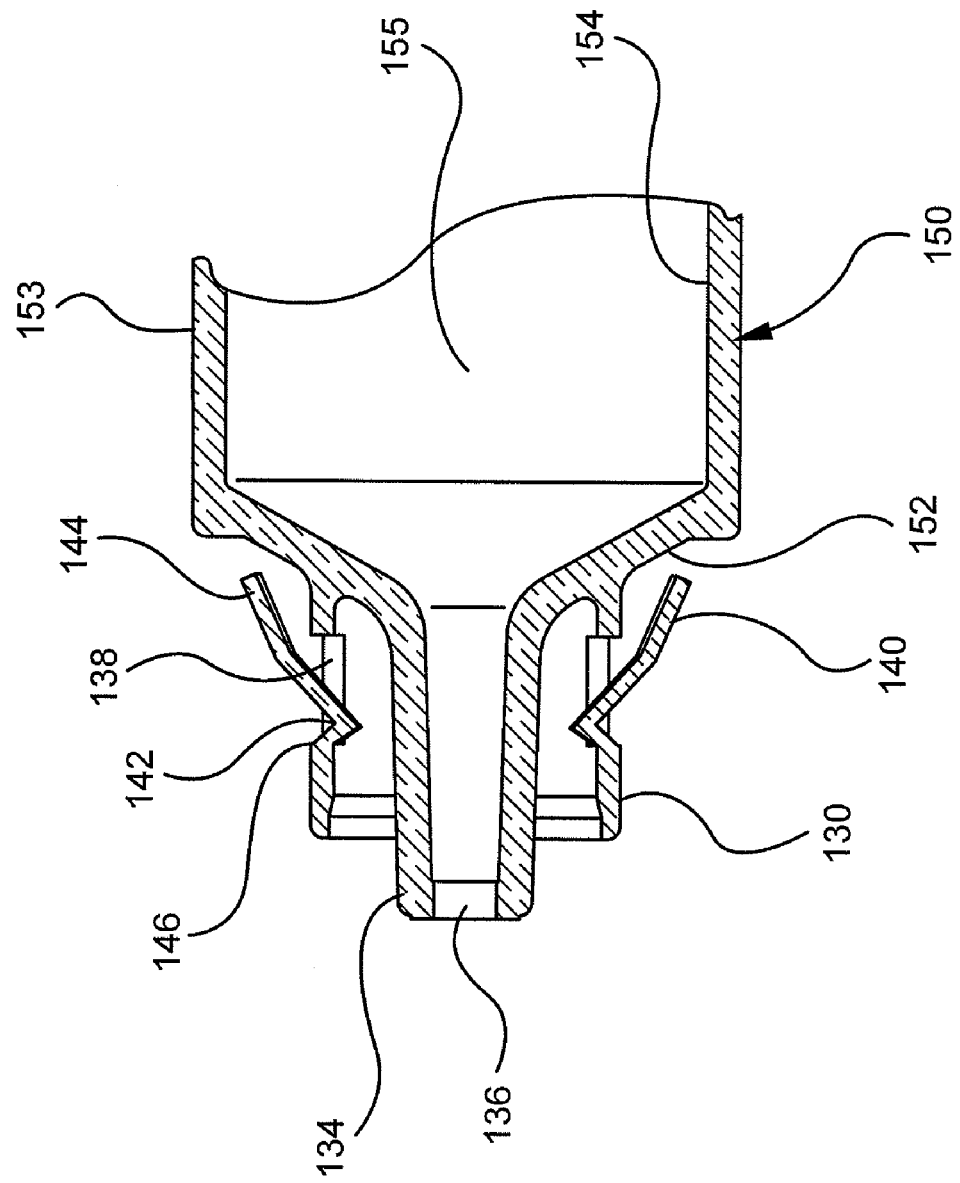
FIG. 5 is an enlarged cross-sectional view of the distal end of the barrel shown in FIG. 1 taken along line 5-5.

To release the portion of the needle hub 124, a radial force may be applied to the arm portion 144. As shown in FIG. 5, application of an outwardly directed radial force or an application of a radial force in a direction away from the luer tip 134 on the arm portion 144 permits removal of the needle hub 120 from the latch 142 by permitting movement of the portion of the needle hub 124 in the distal direction. It will be understood that, removal of the needle hub 120 from the barrel 150 may also be permitted upon application of an inwardly directed radial force or a radial force in a direction toward the luer tip 134.

Optionally, the arm portion 144 may be dimensioned and spaced from the distal wall 142 to prevent application of a radially outwardly directed force to the arm portion 144 and/or to prevent access to the arm portion 144 by a user. In such embodiments, once the needle hub 120 is engaged to the latch 142 or engaged with the barrel 150 in a snap-fit relationship, removal of the needle hub 120 or disengagement of the latch 142 from the needle hub 120 and reuse of a syringe is not permitted.

Figure 6:
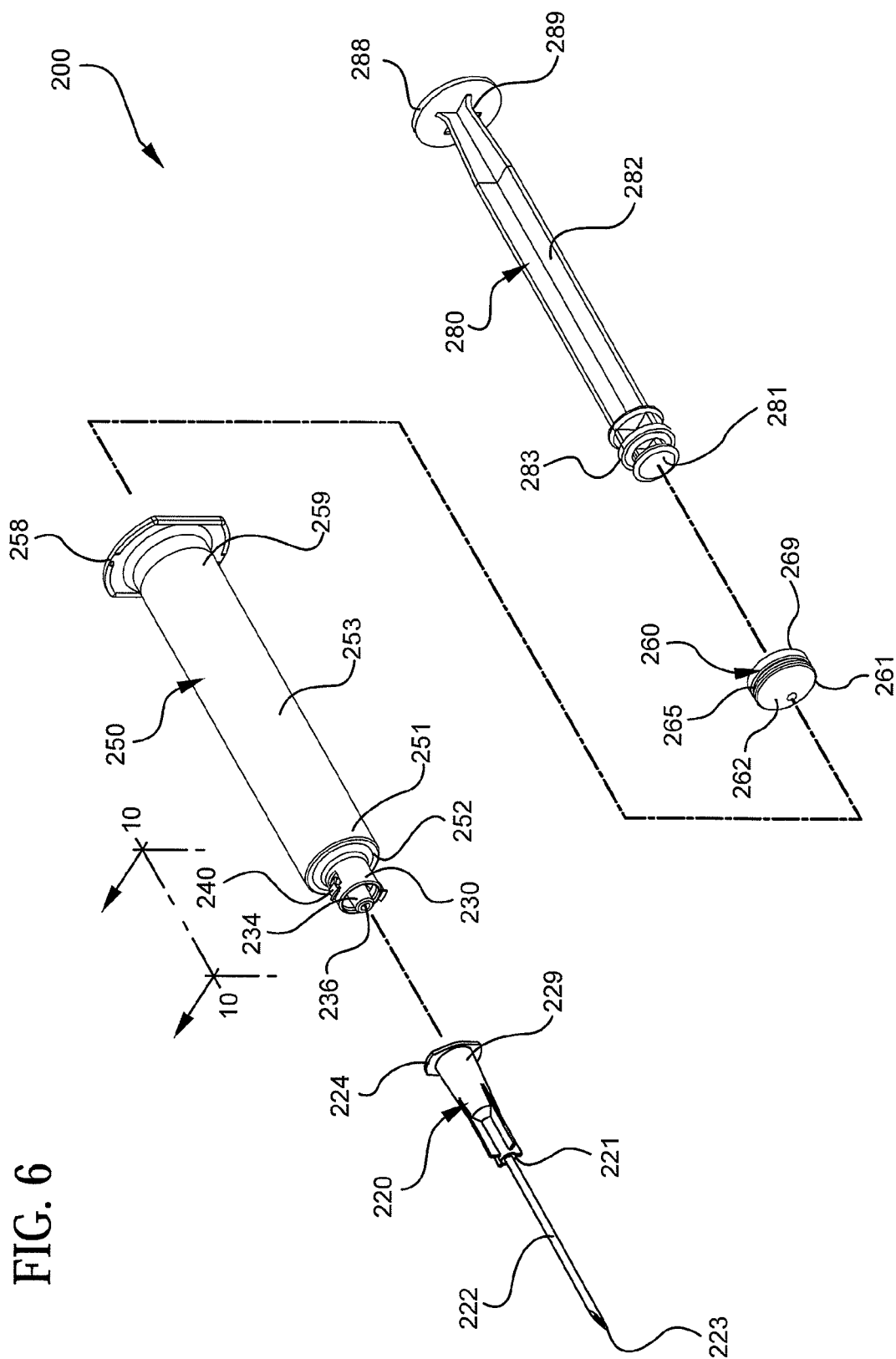
FIG. 6 illustrates a disassembled perspective view of a syringe according to an alternative embodiment of the invention.
Figure 7:
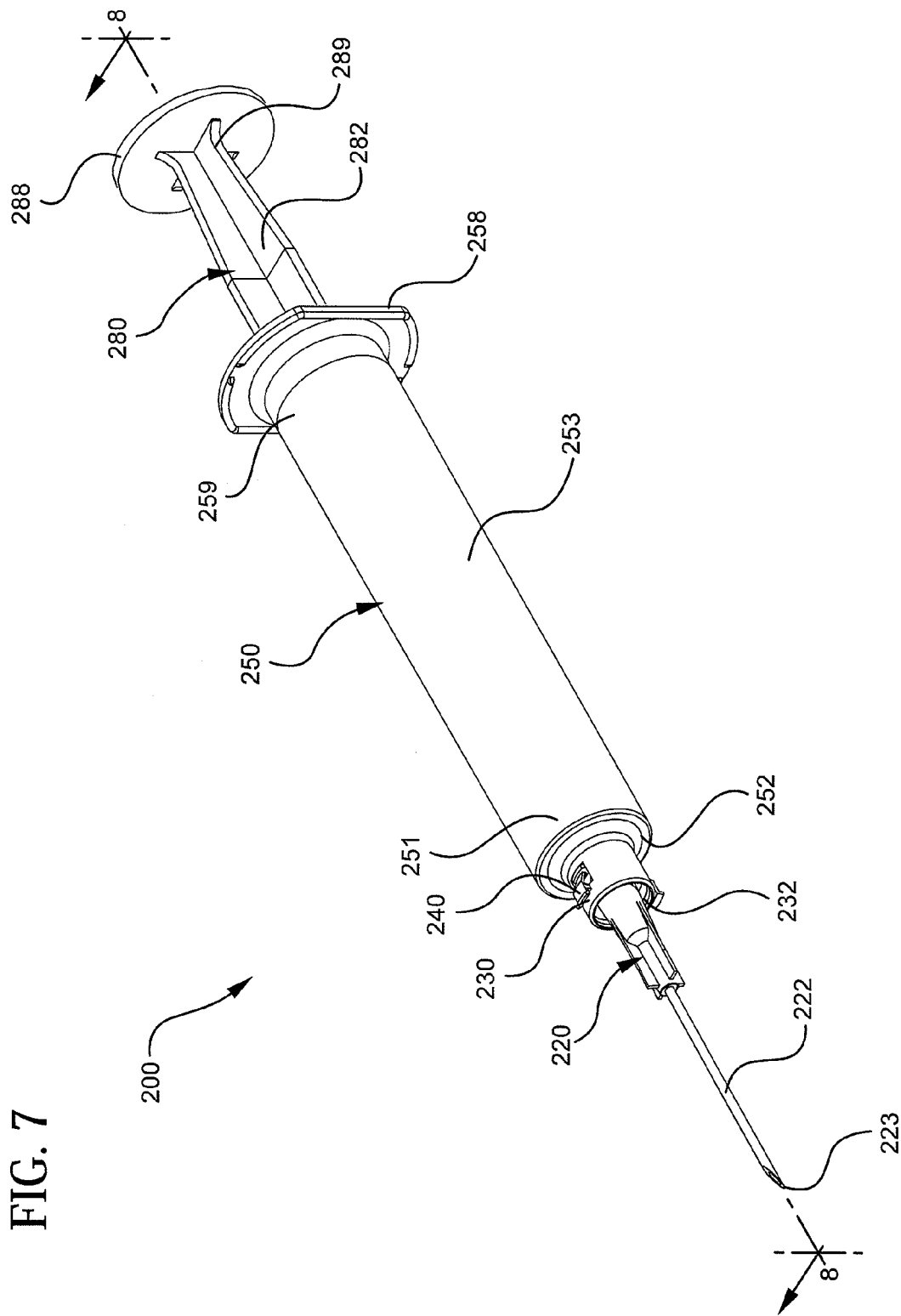
FIG. 7 illustrates a perspective assembled view of the syringe assembly of FIG. 6.
Figure 8:
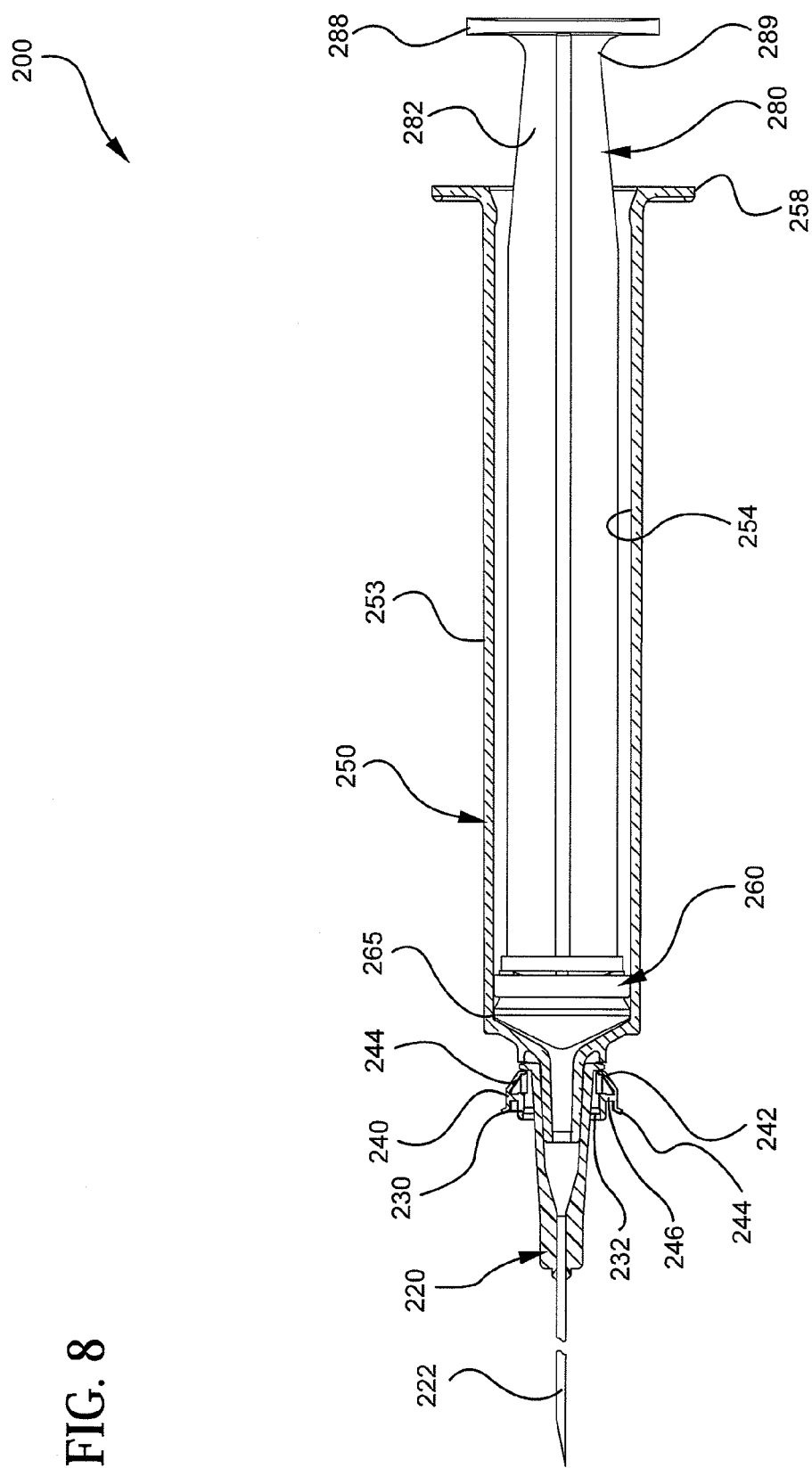
FIG. 8 shows a cross-sectional view of the syringe assembly shown in FIG. 7 taken along line 8-8.
Figure 9:
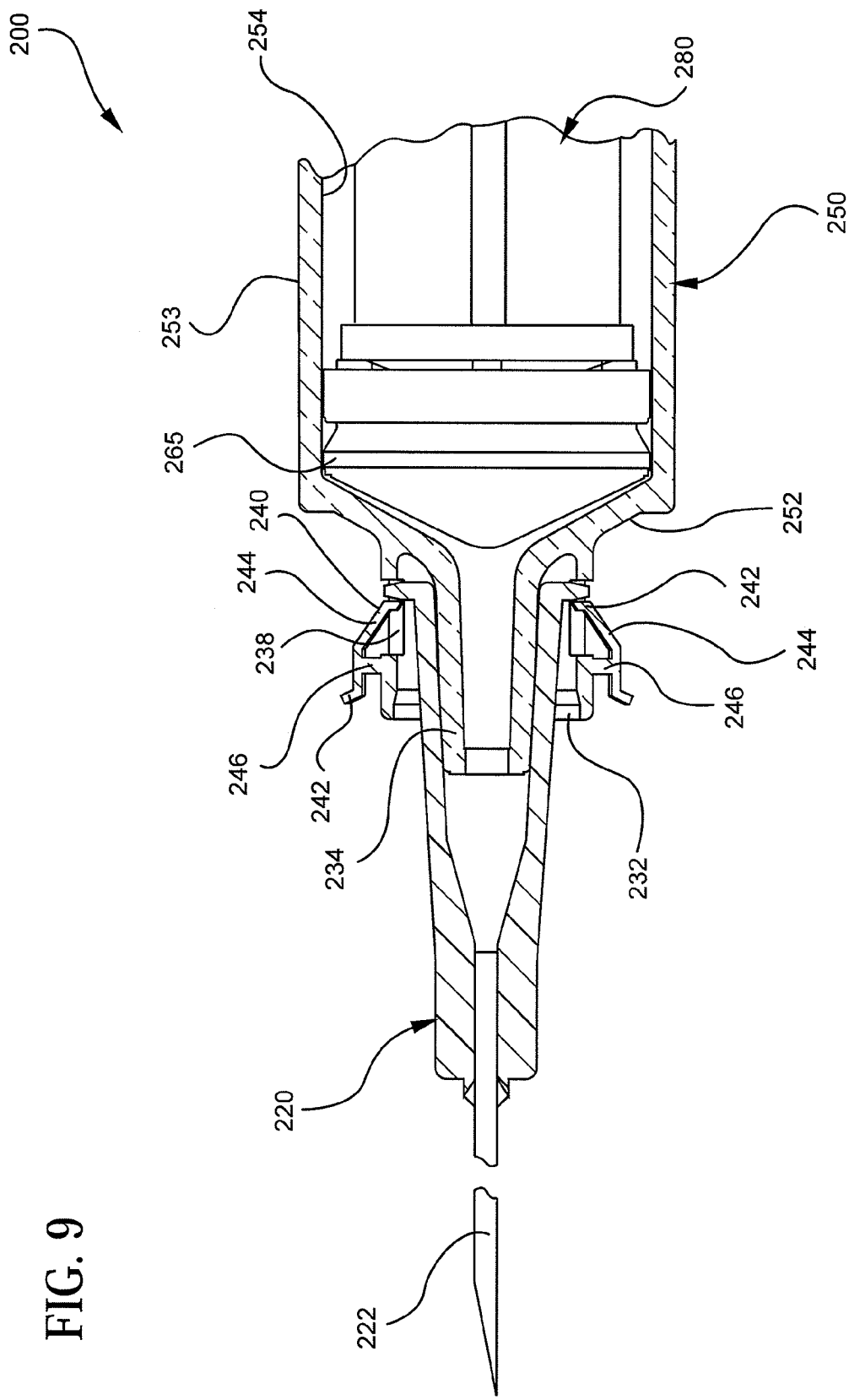
FIG. 9 is an enlarged view of a portion of the barrel shown in FIG. 8.
Figure 10:
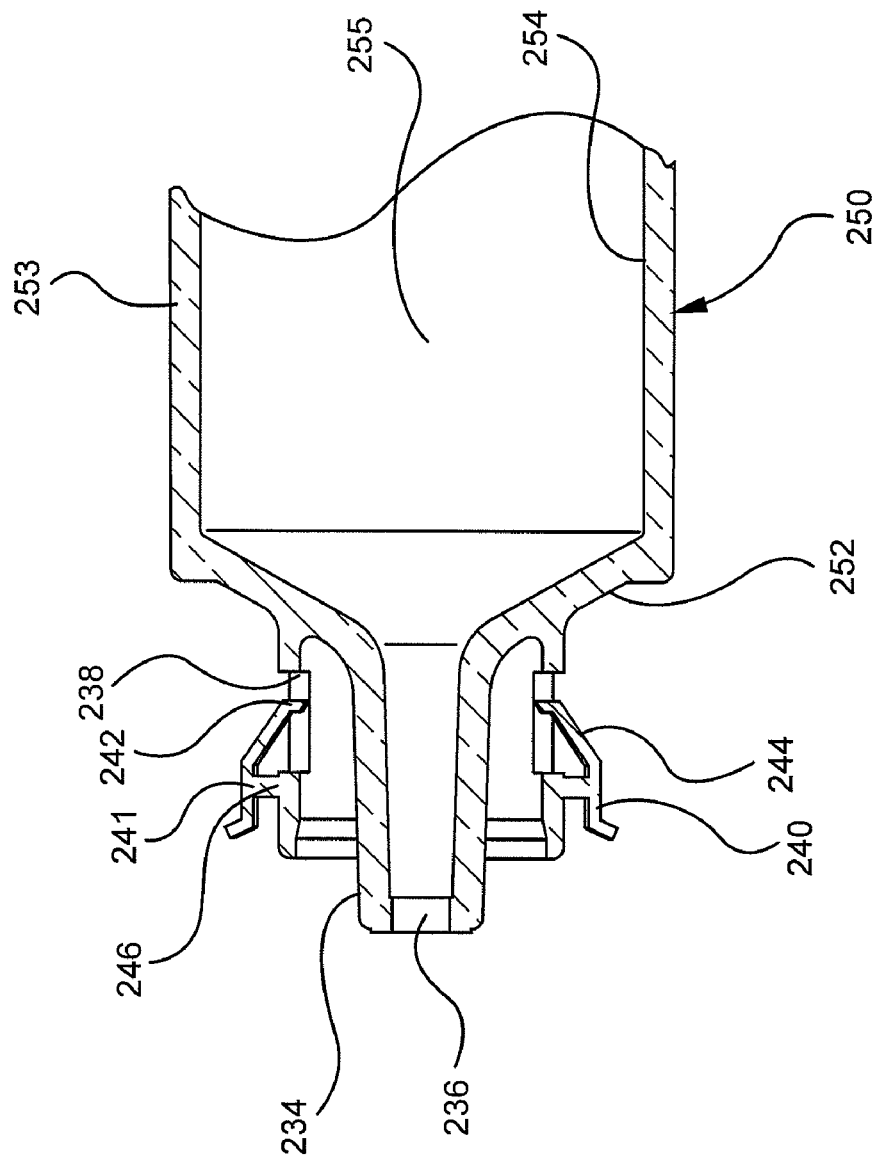
FIG. 10 is a cross-sectional view of the distal end of the barrel shown in FIG. 6 taken along line 10-10.

FIG. 6 shows a second embodiment of a syringe according to the present invention. As with the embodiment shown in FIG. 1, the syringe assembly 200 includes a barrel 250, plunger rod 280 and a separate stopper 260, arranged such that the proximal end of the stopper 269 is attached to the distal end 281 of the plunger rod. The connected stopper 260 and plunger rod 280 are inserted into the proximal end 259 of the barrel 250. An optional standard luer fitting 220 may be attached to the distal end 241 of the barrel.

As more clearly shown in FIGS. 7-10, the barrel 250 includes a sidewall 253 with an inside surface 254 that defines a chamber 255. The barrel 250 includes an open proximal end 259, a distal end 251 and a distal wall 252. The distal wall 252 includes a luer tip 234 with an aperture 236. The distal wall 252 also includes a sleeve 230 in coaxial relationship with the luer tip 234 and defining a cavity 232 with the luer tip 234. The sleeve 230 further includes a peripheral opening 238. The syringe barrel 250 is shown as also having a pair of finger grips 258 attached at the proximal end 259.

The plunger rod 280 shown in FIG. 6 includes proximal end 289, a distal end 281 and a main body 282 extending between the proximal end 289 to the distal end 281. The plunger rod 280 further includes a thumb press 288 at the proximal end 289 of the plunger rod 280. The distal end 281 of the plunger rod may include a stopper engagement portion 283 for attaching the stopper 260 to the distal end 281 of the plunger rod. The stopper 260 shown in FIG. 6 includes a distal end 261, a proximal end and a stopper wall 262 and sealing perimeter 265 at the distal end 261 of the stopper 260.

The syringe may include means for attaching or attachment of a needle hub or standard luer fitting to the barrel in a snap-fit relationship. Examples of suitable means for attaching include a universal connection (not shown), which may also include an optional means for releasing (not shown) the standard luer fitting from the barrel.

The means for attaching a needle hub or standard luer fitting to a barrel may also include a rotatable arm. The rotatable arm may include a first class lever having a fulcrum located between the point at which a force is applied and the point at which a resulting force is exerted. For example, a first class lever may include a bar having two opposite ends attached to a fulcrum so that the two ends remain free. Application of a force on one end of the bar causes the bar to swing or rotate about the fulcrum, and a resultant force is exerted by the opposite end of the bar.

In FIGS. 6-10, the rotatable arm 240 is in the form of a torsional snap-fit element 241. The torsional snap-fit element 241 includes a latch 242 extending into the peripheral opening 238, when in a relaxed or stress-free state. As shown in FIGS. 6-10, the arm portion is in the form of a torsion bar 244, which connects to a latch 242. The torsion bar 244 is also attached to a pivot portion, which is shown in the form of a fulcrum portion 246.

As will be understood by one of ordinary skill in the art, application of a force to the torsion bar 244 causes the torsion bar 244 and latch 242 to rotate around the fulcrum portion 246. This rotation allows the latch 242 to rotate radially outwardly from the peripheral opening 238 and permits the standard luer fitting to proceed past the latch 242. When the force applied to the torsion bar 244 is released or removed, the latch 242 and the torsion bar 244 return to their initial positions or to a relaxed or stress-free state.

The optional standard luer fitting 220 shown in FIG. 6 includes an open proximal end 229 and a distal end 221, which includes a needle cannula 222 having a lumen 223. The open proximal end 229 of the standard luer fitting includes an extending lip 224. As more clearly shown in FIGS. 8 and 9, when assembled in a snap-fit relationship, the open proximal end 229 of the standard luer fitting moves into the cavity 232, proximally past the latch 242 of the torsional snap-fit element 240 and into the peripheral opening 238. As otherwise described herein, application of a radially inwardly directed force on the torsion bar 244 causes the latch 242 and torsion bar 244 to rotate around the fulcrum portion 246 as the extending lip 224 moves past the latch 242. After movement of the extending lip 224 proximally past the latch 242, the force applied to the torsion bar 244 is released and the latch 242 and the torsion bar 244 return to their initial position, with the latch 242 positioned proximally adjacent to the extending lip 224. In accordance with one or more embodiments, this initial rotation and return to an initial position provides tactile indication and/or audible indication of the snap-fit relationship between the standard luer fitting 220 and the barrel 250.

After assembly of the snap-fit relationship, the latch 242 prevents movement of the extending lip 224 of the standard luer fitting in the distal direction. The rotatable arm may be configured to permit removal of the standard luer fitting 220 after establishment of the snap-fit relationship. To release the standard luer fitting 220 from the snap-fit relationship with the barrel 250, a force is be applied on the arm portion 244 to cause the latch 242 and torsion bar 244 to rotate around the fulcrum 246 and permit the extending lip 224 to move distally past the latch 242. Alternatively, the rotatable arm may be configured to remain in a locked position and prevent removal of the standard luer fitting 220 from the barrel.

An additional embodiment of a means for attaching the standard luer fitting and barrel is shown in FIGS. 11-15. In this embodiment, the means includes a rotatable arm with an arm portion in the form of a tab 344 attached at one end to a pivot portion in the form of a connection point 346. The tab 344 further includes a latch 342 at the end opposite the connection point 346.

Figure 11:
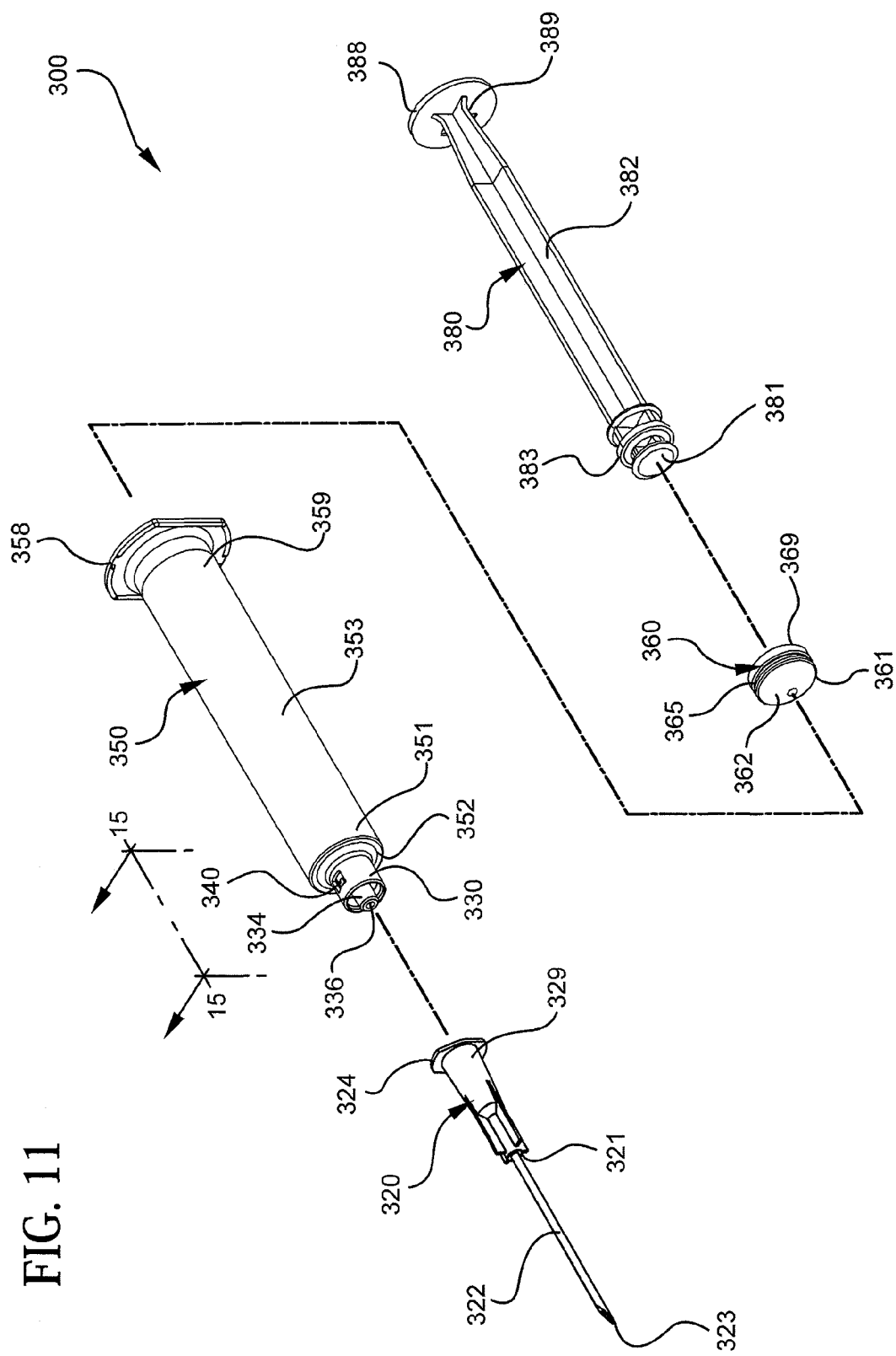
FIG. 11 illustrates a disassembled perspective view of a syringe according to an alternative embodiment of the invention.
Figure 12:
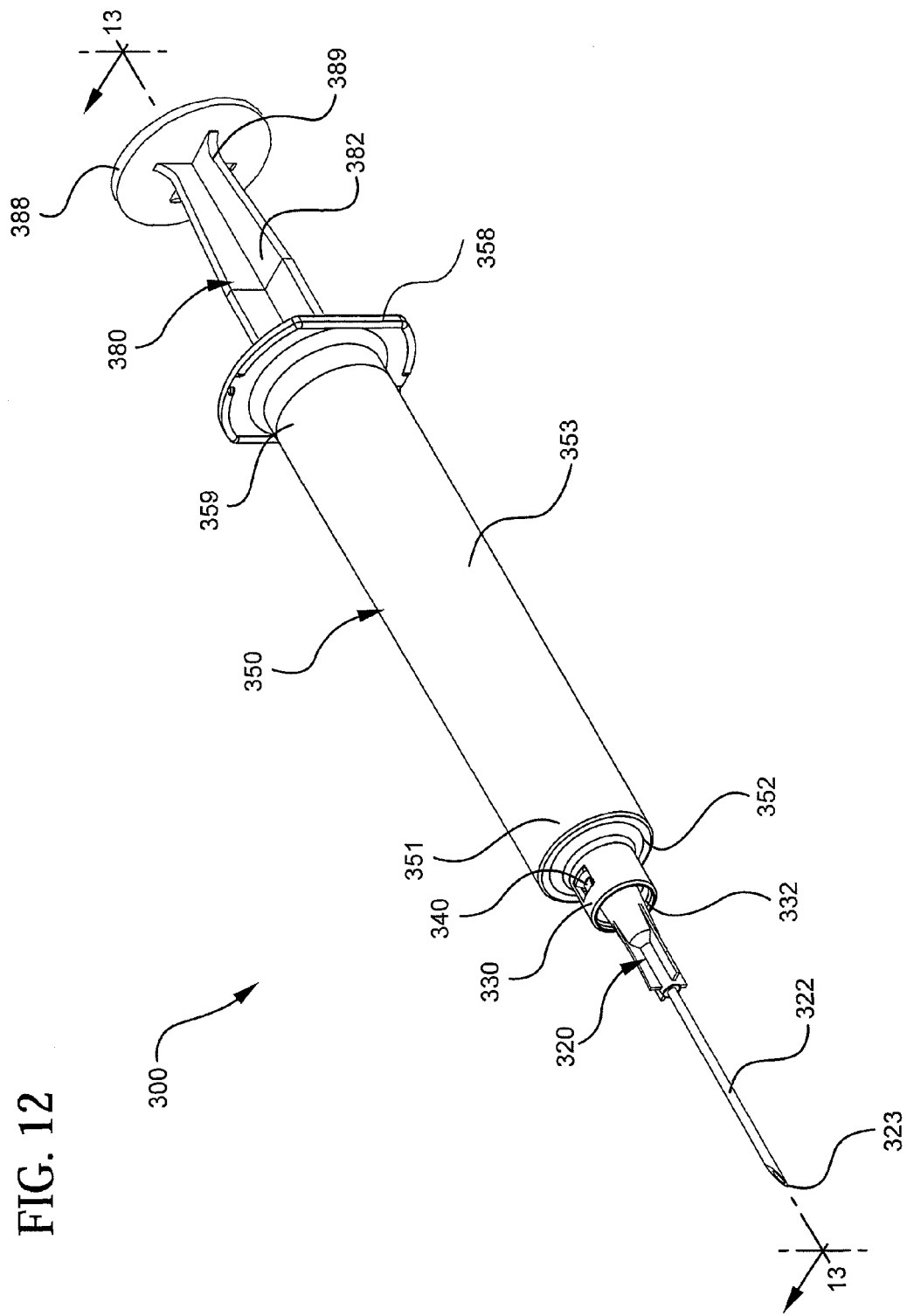
FIG. 12 illustrates a perspective assembled view of the syringe assembly of FIG. 11.
Figure 13:
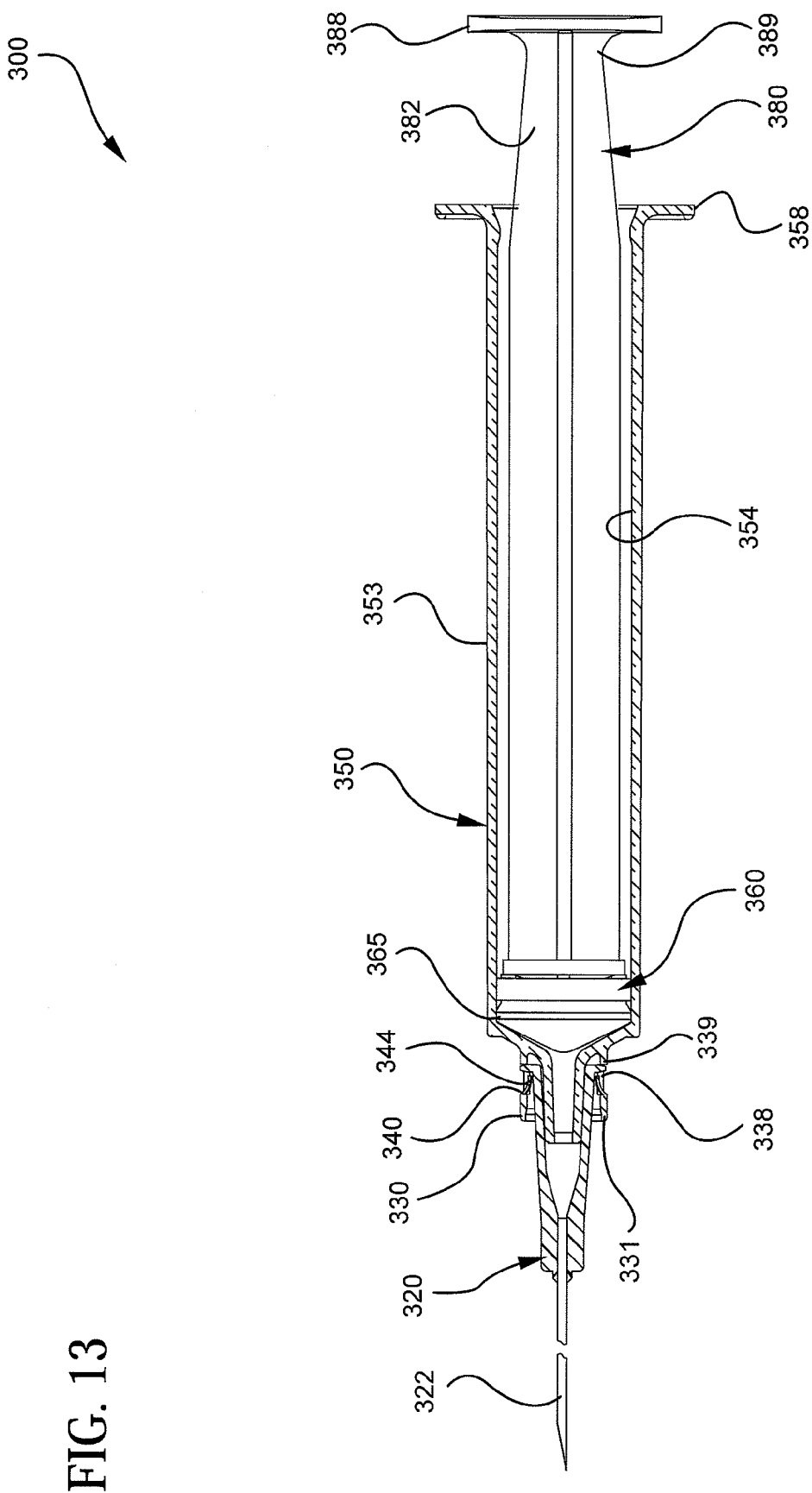
FIG. 13 shows a cross-sectional view of the syringe assembly shown in FIG. 12 taken along line 13-13.
Figure 14:
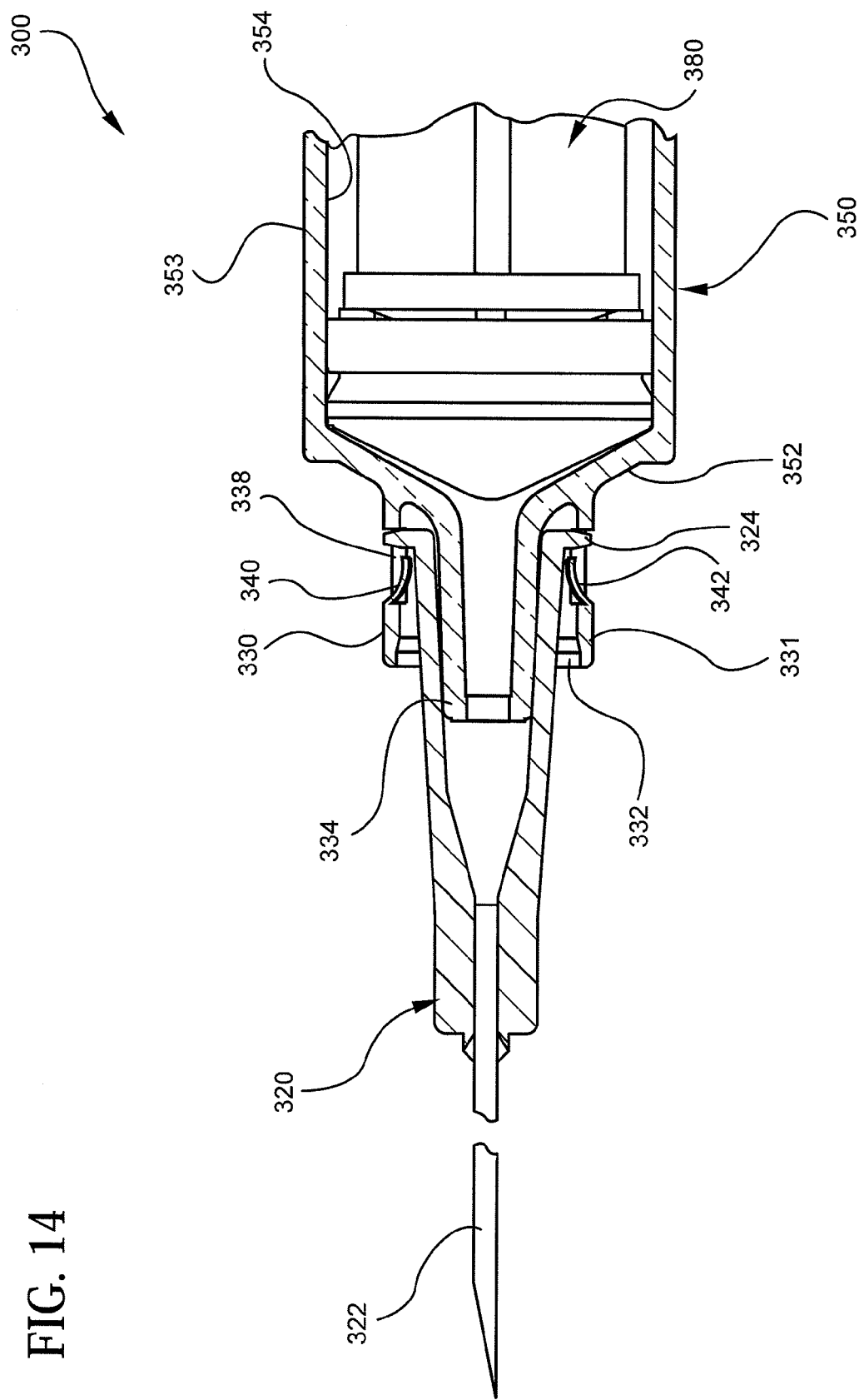
FIG. 14 is an enlarged view of a portion of the barrel shown in FIG. 13.
Figure 15:
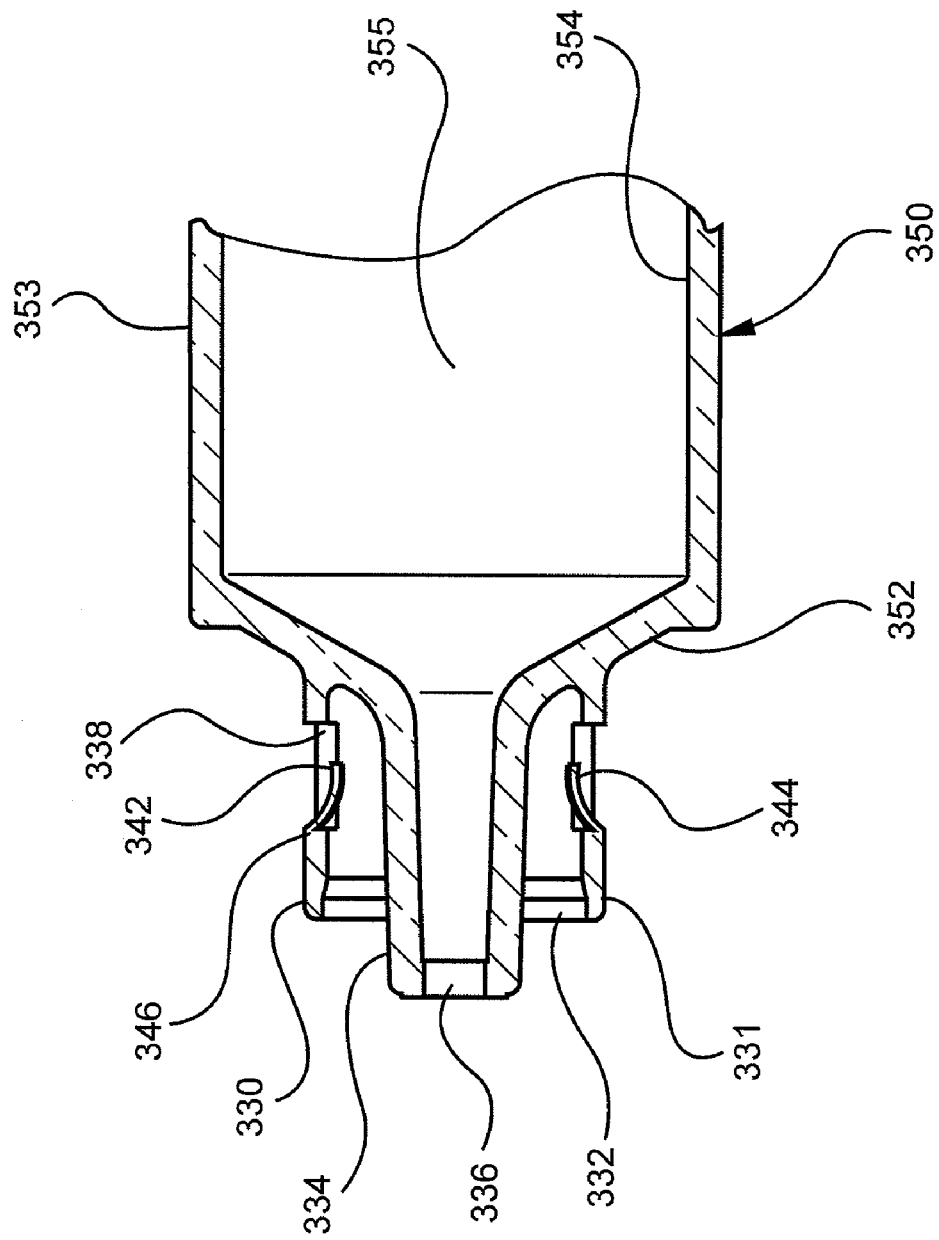
FIG. 15 is a cross-sectional view of the distal end of the barrel shown in FIG. 11 taken along line 15-15.

FIG. 11 shows a syringe assembly 300 having a barrel 350, plunger rod 380 and a stopper 360, arranged such that the proximal end of the stopper 369 is attached to the distal end 381 of the plunger rod. The connected stopper 360 and plunger rod 380 are inserted into the proximal end 359 of the barrel 350.

The barrel 350 has a cylindrical sidewall 353 with an inside surface 354 that defines chamber 355. The barrel 350 includes an open proximal end 359, a distal end 351 and a distal wall 352. The distal wall 352 includes a luer tip 334 with an opening 346. The distal wall 352 also includes a coaxial collar 330 surrounding the luer tip 334 and defining a peripheral recess 332. The syringe barrel 350 includes optional flanges 258 attached at the proximal end 359.

The plunger rod 380 shown in FIG. 11 includes proximal end 389, a distal end 381 and a main body 382 extending between the proximal end 389 to the distal end 391. The plunger rod 380 further includes a thumb press 388 at the proximal end 389 of the plunger rod 380. The distal end 381 of the plunger rod may include a stopper engagement portion 383 for attaching the stopper 360 to the distal end 381 of the plunger rod. The stopper 360 shown in FIG. 11 includes a distal end 361, a proximal end and a stopper wall 362 and seal 365 at the distal end 361 of the stopper 360.

As more clearly shown in FIGS. 12-15, the optional means for attaching the standard luer fitting and barrel includes coaxial collar 330 having distal end 331 and a proximal end 339 having a open slot 338 disposed between the distal end 331 and the proximal end 339. The coaxial collar 330 further includes a first interior surface and a second interior surface. A rotatable arm 340 projects from the first interior surface of the coaxial collar 330 into peripheral recess 332 and open slot 338. The second interior surface includes no projection or impediment extending into the channel. As shown in FIGS. 11-15, the arm portion of the rotatable arm 340 includes a radially inwardly projecting or extending tab 344. The tab 344 is connected to the coaxial collar 330 at a pivot portion, which includes a connection point 346. The tab 340 is rotatable or deflectable at the connection point 346 and includes latch feature 342 at its proximal end. As shown, the tab 344 is not user actuated and cannot be used to disengage the needle hub from the barrel.

For assembly, the needle hub 320 enters the peripheral recess 332 such that the extending lip 324 is aligned with the first interior surface or with the tab 340. As the needle hub 320 moves into the peripheral recess 332, the extending lip 324, the tab 340 is deflected at the connection point 344 and the needle hub 320 is permitted to move fully into the peripheral recess 332 and extend radially outwardly through the open slot 338. Where a third class lever is utilized for the rotatable arm 340, the movement of the extending lip 324 into the peripheral recess 332 exerts a force on the tab 344 between the latch 342 and the connection point 346. The resulting force deflects the tab 344 and the latch 342, permitting the extending lip 324 to advance proximally past the latch 342. This movement of the extending lip 324 proximally past the tab 344 provides tactile and audible indication to the user. While aligned with the first interior surface, the latch 342 prevents movement of the extending lip 324 in the distal direction.

To remove the needle hub 320, the standard luer fitting 320 is rotated relative to the coaxial collar 330 and to align the extending lip 324 with the second interior surface, which is free of any impediment to movement of the extending lip 324 in the distal direction. Such alignment would permit removal of the needle hub 320 from the barrel. As shown in FIGS. 11-15, rotation of the needle hub relative to the barrel or coaxial collar is up to 90 degrees. Alternatively, the rotation of the needle hub relative to the barrel may be up to 180 degrees. The needle hub 230 may then be removed from the peripheral recess 332.

The syringe of FIGS. 11-15 may be structured to also prevent reuse thereof after the needle hub has been attached to the barrel in a snap-fit relationship. For example, upon assembly of the needle hub 320 to the barrel, extension of the extending lip 324 through the open slot 338 of the coaxial collar 330 prevents rotation of the needle 320 relative to the coaxial collar 330 and, thereby prevents removal thereof. The rotatable arm 340 may also be dimensioned and/or positioned to prevent user actuation and, once the needle hub is attached in a snap-fit relationship with the barrel, to prevent disengagement thereof.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe comprising:
   a barrel including a sidewall having an inside surface defining a chamber for retaining fluid, an open proximal end and a distal end including a distal wall having a luer tip with an opening therethrough in fluid communication with said chamber;
   a collar extending from the distal wall, the collar in a coaxial relationship with the luer tip defining a channel for receiving a needle hub therein and having a distal end and a proximal end with an open slot disposed therebetween;
   a rotatable arm extending from the collar including a pivot portion, an arm portion extending radially outwardly from the pivot portion and a latch extending radially inwardly from the pivot portion for engagement with a lip portion of the needle hub to permit assembly of the needle hub and the collar in a snap-fit relationship without relative rotation between the needle hub and the barrel, wherein upon engagement of the pivot portion of the rotatable arm with the lip portion of the needle hub the lip portion extends through the open slot of the collar to prevent rotation of the needle hub relative to the collar; and
   an elongate plunger rod including a proximal end, a distal end having a stopper and an end wall, the stopper in a fluid-tight engagement with the inside surface of the barrel, and a main body extending between the proximal and distal end, the plunger rod being distally and proximally movable within said chamber.

2. The syringe of claim 1, wherein the channel is configured to receive an open proximal end of the needle hub and, upon assembly of the needle hub and collar, to engage the open proximal end with the rotatable arm to prevent removal of the hub from the collar.

3. The syringe of claim 2, wherein, when the hub and the collar are assembled, the rotatable arm and open proximal end are configured such that the application of an inwardly directed radial force on the arm permits removal of the hub from the collar.

4. The syringe of claim 2, wherein, when the hub and the collar are assembled, the rotatable arm and open proximal end are configured such that the application an outwardly directed radial force on the rotatable arm permits removal of the hub from the collar.

5. The syringe of claim 1, wherein, when the hub and collar are assembled, the rotatable arm provides an audible indication of the snap-fit engagement of the hub and the collar.

6. The syringe of claim 1, wherein, when the hub and collar are assembled, the rotatable arm provides a tactile indication of the snap-fit engagement of the hub and the collar.

7. The syringe of claim 1, wherein the rotatable arm comprises a torsional snap-fit element.

8. The syringe of claim 7 further comprising a hub including an open proximal end and an outwardly extending lip disposed on the open proximal end, the outwardly extending lip positioned to engage the torsional snap-fit element.

9. The syringe of claim 8, wherein, upon advancement of hub into the channel, the outwardly extending lip advances past the torsional snap-fit element and the torsional snap-fit element prevents movement of the outwardly extending lip in a distal direction.

10. The syringe of claim 9, wherein, application of an inwardly directed radial force on the torsional snap-fit element permits movement of the outwardly extending lip in the distal direction.

11. The syringe of claim 9, wherein the torsional snap-fit element provides tactile indication of the advancement of the outwardly extending lip past the torsional snap-fit element.

12. The syringe of claim 9, wherein the torsional snap-fit element provides audible indication of the advancement of the outwardly extending lip past the torsional snap-fit element.

13. A packaged medical device comprising:
- a needle hub comprising an open proximal end and a distal end including a needle; and
- a syringe according to claim 1, the needle hub and the syringe contained in a single package.

14. The syringe of claim 1, wherein the rotatable arm comprises a third class lever.

* * * * *